(12) United States Patent
Curley et al.

(10) Patent No.: US 11,938,013 B2
(45) Date of Patent: Mar. 26, 2024

(54) OBSCURING COVER FOR COVERING AT LEAST A PORTION OF A SAW

(71) Applicant: MEDSTAR HEALTH, INC., Columbia, MD (US)

(72) Inventors: Andrew Curley, Great Falls, VA (US); Nicholas Jarboe, Washington, DC (US); Daniel Choi, Philadelphia, PA (US)

(73) Assignee: MEDSTAR HEALTH, INC., Columbia, MD (US)

( * ) Notice: Subject to any disclaimer, the term of this patent is extended or adjusted under 35 U.S.C. 154(b) by 71 days.

(21) Appl. No.: 17/666,629

(22) Filed: Feb. 8, 2022

(65) Prior Publication Data

US 2023/0248590 A1    Aug. 10, 2023

(51) Int. Cl.
*A61F 15/02*    (2006.01)

(52) U.S. Cl.
CPC .................................. *A61F 15/02* (2013.01)

(58) Field of Classification Search
CPC ........................................................ A61F 15/02
USPC .................................................. 30/390; 83/23
See application file for complete search history.

(56) References Cited

U.S. PATENT DOCUMENTS

| | | | | |
|---|---|---|---|---|
| 1,876,337 A * | 9/1932 | Mead | ....................... | A61F 15/02 30/344 |
| 2,518,939 A * | 8/1950 | Ross | ....................... | A61F 15/02 30/390 |
| 2,898,957 A * | 8/1959 | Demarkis | .................. | B27C 5/10 144/136.95 |
| 4,412,381 A * | 11/1983 | Kirk | ....................... | B23D 59/006 30/377 |
| 4,611,585 A * | 9/1986 | Steidle | ..................... | A61F 15/02 30/124 |
| 4,993,243 A * | 2/1991 | Guinn | ..................... | B23Q 11/06 69/37 |
| 5,012,582 A * | 5/1991 | Bristol | ................... | B23D 45/16 30/504 |
| 5,702,415 A * | 12/1997 | Matthai | ..................... | B27B 5/32 606/178 |
| 6,561,063 B1 * | 5/2003 | Mulford | ................. | B24B 55/052 451/354 |
| 6,678,960 B2 * | 1/2004 | Williams | .................. | B27B 5/08 30/373 |
| 6,925,917 B2 * | 8/2005 | Tilley | ...................... | B23D 59/02 606/82 |

(Continued)

Primary Examiner — Omar Flores Sanchez
(74) Attorney, Agent, or Firm — TAROLLI, SUNDHEIM, COVELL & TUMMINO L.L.P.

(57) ABSTRACT

An obscuring cover for covering at least a portion of a saw that includes a saw body and a saw blade attached to the saw body is provided. The obscuring cover includes an interior cavity defined by at least one inner surface of the obscuring cover. The interior cavity is configured to removably receive at least a portion of the saw body. At least one securing member is at least partially located at least one of internal to and adjacent to the interior cavity. The at least one securing member is configured to removably engage an exterior portion of the saw to removably connect the obscuring cover to the saw. At least a portion of the obscuring cover is configured to at least partially visually obstruct a subject's view of the saw blade when the obscuring cover is connected to the saw.

19 Claims, 7 Drawing Sheets

(56) References Cited

U.S. PATENT DOCUMENTS

| | | | | |
|---|---|---|---|---|
| 8,302,519 | B2* | 11/2012 | McCracken | B23D 47/08 30/392 |
| 10,201,864 | B2* | 2/2019 | Rubens | B25F 5/00 |
| 2010/0024223 | A1* | 2/2010 | Lehman | A61F 15/02 30/374 |
| 2012/0005904 | A1* | 1/2012 | Zwirkoski | B23D 61/02 83/13 |
| 2022/0402049 | A1* | 12/2022 | Horn | B23D 59/001 |

* cited by examiner

OBSCURING COVER FOR COVERING AT LEAST A PORTION OF A SAW

TECHNICAL FIELD

This disclosure generally relates to an obscuring cover for covering at least a portion of a saw, a cast removal kit, and a method for removing a cast from a subject. More particularly, this disclosure relates to an obscuring cover for covering at least a portion of a saw, a cast removal kit that includes an obscuring cover and a cast saw, and a method for removing a cast from a subject that includes connecting an obscuring cover to a cast saw.

BACKGROUND

It is relatively common for a person to endure a fracture during their life. Many fractures may be treated nonoperatively, often using a cast for immobilization while the fracture heals. Once the fractural heals, the cast is often removed using a saw, such as a cast saw.

FIG. 1 depicts a known saw 100, e.g., a cast saw, as disclosed in U.S. Pat. No. 5,702,415, issued 30 Dec. 1997 to Matthai et al., the subject matter of which is incorporated herein by reference in its entirety. The cast saw 100 includes a saw body 102 having a saw blade 104 attached thereto. The saw blade 104 may be a toothed blade that is configured to cut through a thickness of a cast to facilitate removal of the cast from a subject. The saw body 102 may contain therein a motor 106 that is actuable to drive an oscillating output drive train 108. When driven, the oscillating output drive train 108 oscillates the saw blade 104 relative to the saw body 102 to place the saw blade 104 in a condition for cutting at least a portion of a cast. The cast saw 100 may also include a protective cover 110 that is attached to the saw body 102 and surrounds at least a portion of the saw blade 104. The protective cover 110 has a mouth 112 within which the saw blade 104 is located. The mouth 112 may be wide enough to provide the saw blade 104 with substantial clearance to oscillate. The protective cover 110 surrounding the saw blade 104 may shield the saw blade 104 so as to at least partially prevent contact between the saw blade 104 and a non-target area. The non-target area may be any area that is not a desirable target to be cut by the cast saw 100, such as, for example, any area on an operator of the cast saw 100, any area on the subject in which the operator is not targeting to cut, any object in a room in which the cast saw 100 is present that the operator is not targeting to cut, any area on the cast saw 100 or other component that is connected to the cast saw 100, any other person or object that the operator is not targeting to cut, or any combination thereof.

Although the protective cover 110 may help prevent unwanted contact with the saw blade 104, the protective cover 110 leaves portions of the saw blade 104 visible to the subject/patient during a cast removal procedure. Certain patient populations, such as children, may be fearful of the saw blade's 104 metal teeth. Those fearful patients may cry or undesirably move during their cast removal, which may lengthen or disrupt the cast removal process. The cast removal process may thus be frustrating and emotionally fraught for the patient, as well as a member of the patient's support group (e.g., the patient's parent(s) or legal guardian (s)) and the operator(s) of the cast saw 100.

SUMMARY

In an aspect, alone or in combination with any other aspect, an obscuring cover is for covering at least a portion of a saw that includes a saw body and a saw blade attached to the saw body. The obscuring cover includes an interior cavity defined by at least one inner surface of the obscuring cover. The interior cavity is configured to removably receive at least a portion of the saw body. At least one securing member is at least partially located at least one of internal to and adjacent to the interior cavity. The at least one securing member is configured to removably engage an exterior portion of the saw to removably connect the obscuring cover to the saw. At least a portion of the obscuring cover is configured to at least partially visually obstruct a subject's view of the saw blade when the obscuring cover is connected to the saw.

In an aspect, alone or in combination with any other aspect, a cast removal kit includes a cast saw having a saw body, a saw blade attached to the saw body, and a motor actuatable to selectively move the saw blade relative to the saw body for cutting a portion of a cast. The cast saw has a protective cover that is attached to the saw body and surrounds at least a portion of the saw blade so as to at least partially prevent contact between the saw blade and a non-target area. The cast removal kit also includes an obscuring cover. The obscuring cover includes an interior cavity defined by at least one inner surface of the obscuring cover. The interior cavity is configured to removably receive at least a portion of the saw body. At least one securing member is at least partially located at least one of internal to and adjacent to the interior cavity. The at least one securing member is configured to removably engage an exterior portion of the cast saw to removably connect the obscuring cover to the cast saw. At least a portion of the obscuring cover is configured to at least partially visually obstruct a subject's view of the saw blade when the obscuring cover is connected to the cast saw.

In an aspect, alone or in combination with any other aspect, a method for removing a cast from a subject includes providing an obscuring cover for covering at least a portion of a saw. The obscuring cover includes an interior cavity defined by at least one inner surface of the obscuring cover. The interior cavity is configured to removably receive at least a portion of a saw body. At least one securing member is at least partially located at least one of internal to and adjacent to the interior cavity. The at least one securing member is configured to removably engage an exterior portion of the saw to removably connect the obscuring cover to the saw. At least a portion of the obscuring cover is configured to at least partially visually obstruct a subject's view of a saw blade of the saw when the obscuring cover is connected to the saw. A cast saw that includes a saw body and a saw blade attached to the saw body is provided. At least a portion of the saw body is inserted into the interior cavity of the obscuring cover. The obscuring cover is connected to the cast saw by engaging the at least one securing member to an exterior portion of the cast saw. With the obscuring cover connected to the cast saw, the cast is cut with the saw blade. Concurrently with cutting the cast, the subject's view of the saw blade is obstructed with the obscuring cover. The cut cast is removed from the subject.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DESCRIPTION OF EMBODIMENTS

Figure 1:
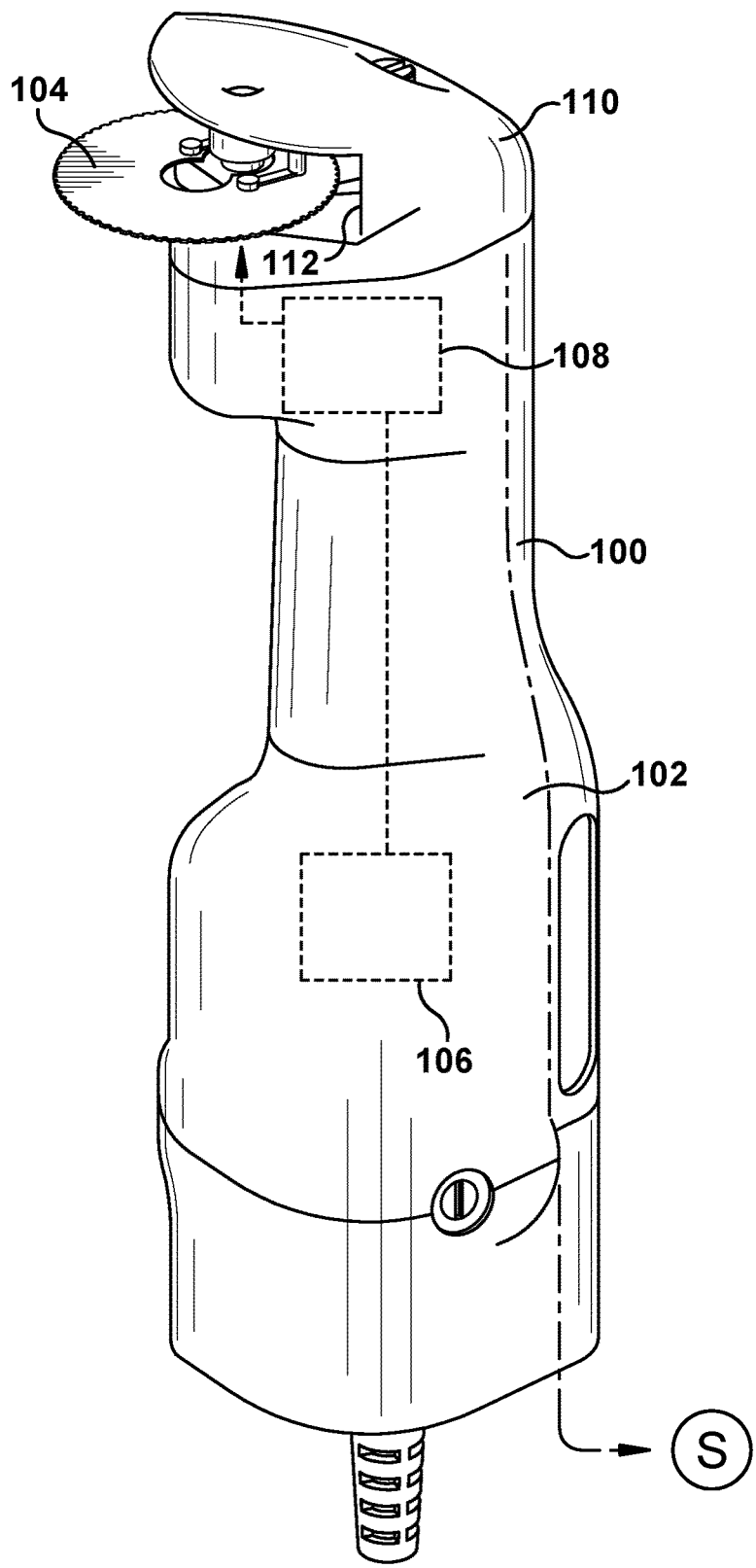
FIG. 1 is a perspective side view of a known cast saw.

Unless defined otherwise, all technical and scientific terms used herein have the same meaning as is commonly understood by one of ordinary skill in the art to which the present disclosure pertains.

As used herein, the terms "patient" or "subject" can be used interchangeably and can refer to any warm-blooded organism including, but not limited to, human beings, pigs, rats, mice, birds, cats, dogs, goats, sheep, horses, monkeys, apes, rabbits, cattle, farm animals, livestock, etc.

As used herein, the term "operator" can be used interchangeably to refer to an individual who prepares for, assists with, and/or performs a procedure or the operation of a tool.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, the phrase "at least one of X and Y" can be interpreted to include X, Y, or a combination of X and Y. For example, if an element is described as having at least one of X and Y, the element may, at a particular time, include X, Y, or a combination of X and Y, the selection of which could vary from time to time. In contrast, the phrase "at least one of X" can be interpreted to include one or more Xs.

It will be understood that when an element is referred to as being "on," "attached" to, "connected" to, "contacting," etc., another element, it can be directly on, attached to, connected to or contacting the other element or intervening elements may also be present. In contrast, when an element is referred to as being, for example, "directly attached" to another element, there are no intervening elements present. It will also be appreciated by those of skill in the art that references to a structure or feature that is disposed "adjacent" another feature may not have portions that overlap or underlie the adjacent feature.

Spatially relative terms, such as "upper" and the like, may be used herein for ease of description to describe one element or feature's relationship to another element(s) or feature(s) as illustrated in the Figures. It will be understood that the spatially relative terms can encompass different orientations of a device in use or operation, in addition to the orientation depicted in the Figures. For example, if a device in the Figures is inverted, elements described as "upper" elements or features would then be "lower" elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or Figures unless specifically indicated otherwise.

The invention comprises, consists of, or consists essentially of the following features, in any combination.

Figure 2:
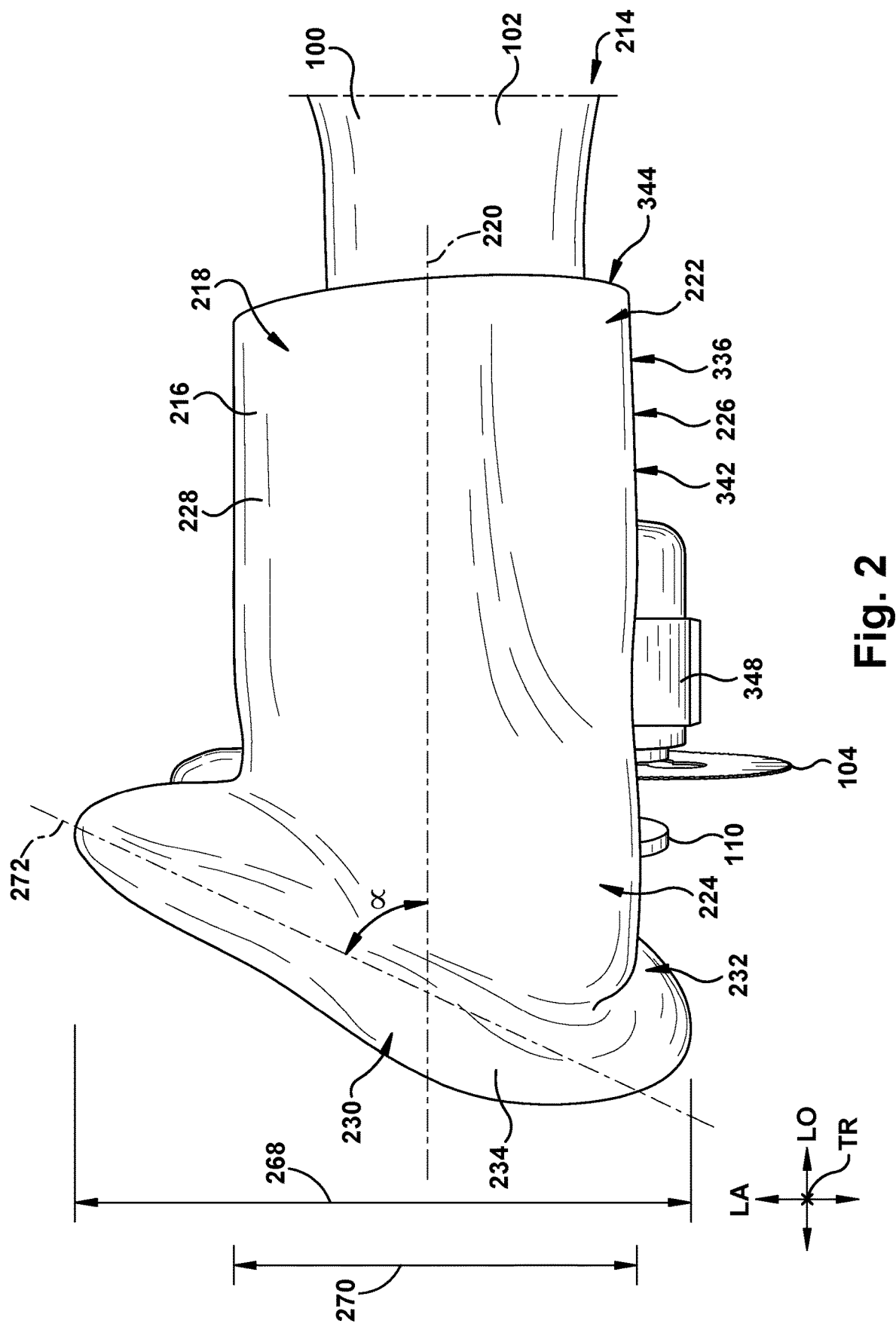
FIG. 2 is a side view of an obscuring cover for covering at least a portion of a saw according to one aspect of the present disclosure, depicting the obscuring cover connected to a portion of the saw.
Figure 3:
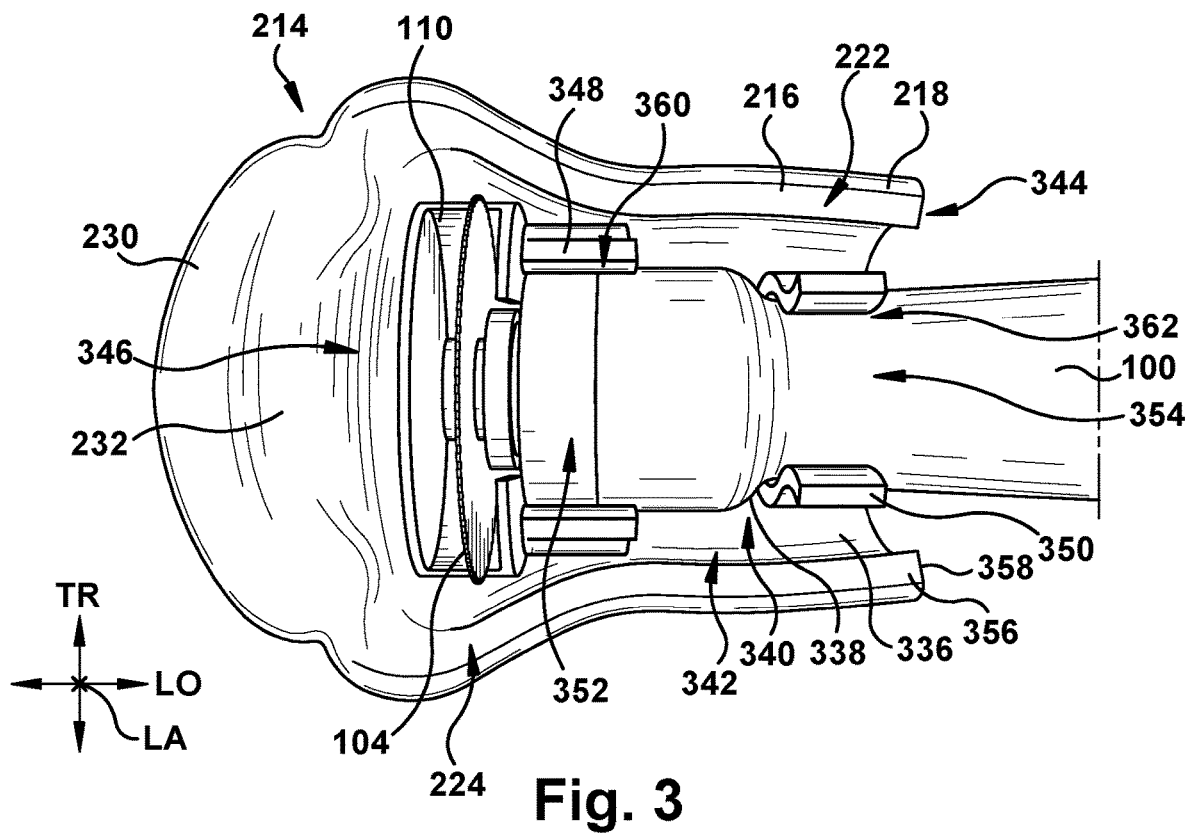
FIG. 3 is a bottom view of the aspect of FIG. 2.
Figure 4:
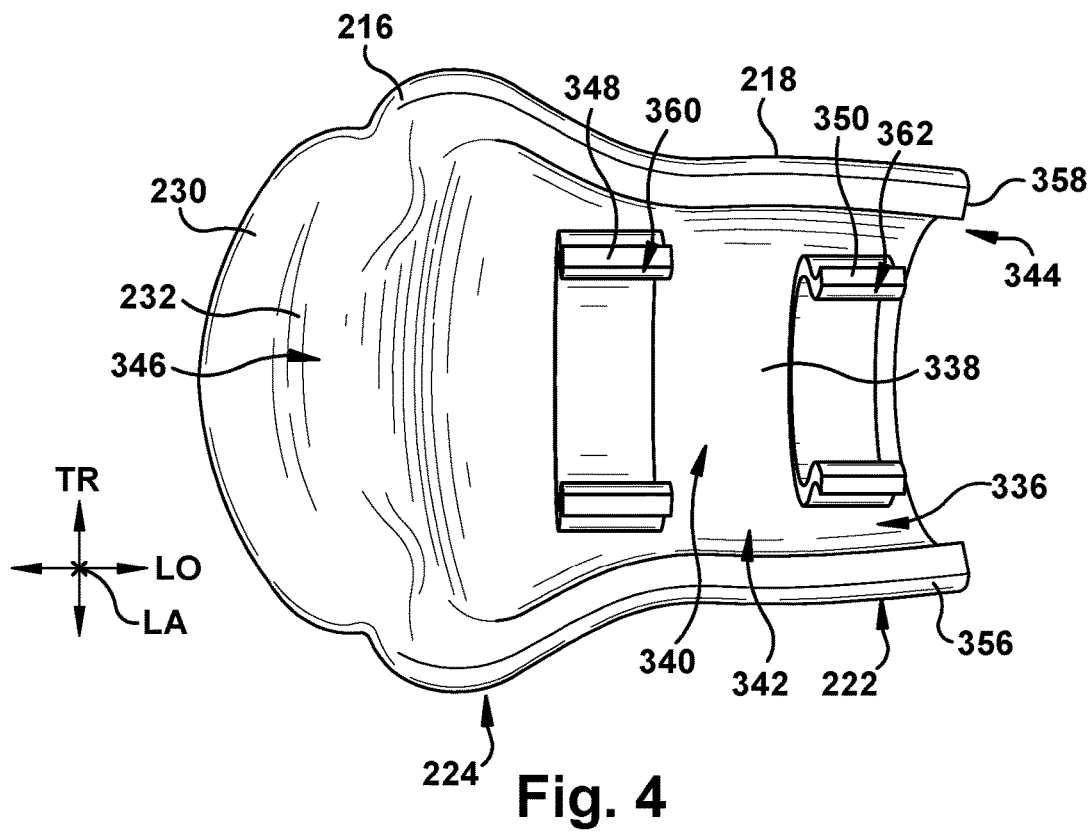
FIG. 4 is a bottom view of the obscuring cover of the aspect of FIG. 1.

FIGS. 2-4 depict an obscuring cover 216 for covering at least a portion of a saw, such as the cast saw 100 of FIG. 1. The obscuring cover 216 may be included in a cast removal kit 214 with the cast saw 100, and may be used by the cast saw operator to help visually obstruct a subject's view of the saw blade 104. The obscuring cover 216 includes a cover body portion 218 that extends along a longitudinal axis 220 of the obscuring cover 216. The term "longitudinal" is used herein to indicate a substantially horizontal direction, in the orientation of FIG. 2, and is indicated as "LO" in FIG. 2. The cover body portion 218 has a proximal body end portion 222 and a distal body end portion 224, with oppositely facing inner and outer body surfaces 226, 228 extending between the proximal and distal body end portions 222, 224.

A cover head portion 230 of the obscuring cover 216 may be longitudinally adjacent to the cover body portion 218 and attached to the distal body end portion 224. The cover head portion 230 and the cover body portion 218 may be mutually connected so as to resist relative movement of the cover head portion 230 and the cover body portion 218. For example, the cover head portion 230 may be directly and fixedly attached to the cover body portion 218, such as by welding, mechanical fasteners, adhesives, or any other attachment scheme or combination thereof, or the cover head portion 230 and the cover body portion 218 may be cast, molded, machined, or otherwise formed from a unitary piece of material. In such a configuration, the cover head portion 230 and the cover body portion 218 may be permanently attached to one another so as to resist relative movement and separation of cover head portion 230 and the cover body portion 218. The cover head portion has oppositely facing inner and outer head surfaces 232, 234. The outer head surface 234 is configured for visual exposure to the subject when the cast saw 100 is in use.

As shown in FIGS. 3-4, the inner head surface 232 and the inner body surface 226 collectively define an interior cavity 336 of the obscuring cover 216. The interior cavity 336 is configured to receive at least a portion of the cast saw 100. For example, the interior cavity 336 may be configured to receive a portion of the saw body 102, a portion of the saw blade 104, and/or a portion of the protective cover 110. However, a portion of the cast saw 100, such as, for example, a portion of the saw blade 104, may extend outward from the interior cavity 336 when received therein. Although interior cavity 336 is configured to receive the cast saw 100 shown in FIG. 1, the interior cavity 336 may be configured so that the interior cavity 336 can receive variety of different saws/cast saws, or may be configured so that the interior cavity 336 can receive one or more specific saws/cast saws.

As shown in FIGS. 3-4, a first or upper portion 338 of the inner body surface 226 at least partially forms a lateral blind end 340 of the interior cavity 336. The term "lateral" is used herein to indicate a direction substantially perpendicular to the "longitudinal" direction, is shown as the vertical direction in the orientation of FIG. 2, and is indicated at "LA" in FIG. 2. As shown in FIGS. 3-4, the lateral blind end 310 is laterally spaced from a lateral cover opening 342 in the obscuring cover 216 through which the interior cavity 336 is accessible. The interior cavity 336 may also be accessible through a longitudinal cover opening 344 in the obscuring cover 216. The longitudinal cover opening 344 is longitudinally spaced from a longitudinal blind end 346 of the interior cavity 336. The longitudinal blind end 346 is at least partially formed by the inner head surface 232.

The cast saw 100 and/or the obscuring cover 216 are configured so that the cast saw 100 is selectively inserted through the lateral cover opening 342 into the interior cavity 336. Alternatively, or additionally, the cast saw 100 and/or the obscuring cover 216 may be configured so that the cast saw 100 can be selectively inserted through the longitudinal cover opening 344 into the interior cavity 336. As shown in FIGS. 2-3, a portion of the saw body 102 may extend through the longitudinal cover opening 344 when a portion of the saw body 102 is received in the interior cavity 336.

As shown in FIG. 3, the saw blade 104 and the protective cover 110 may be adjacent the distal body end portion 224 when the cast saw 100 is received in the interior cavity 336. A longitudinal portion of the cast saw 100 that includes the saw blade 104 and the protective cover 110 may have a greater transverse length than other longitudinal portions of the cast saw 100. The term "transverse" is used herein to indicate a direction substantially perpendicular to the "longitudinal" and "lateral" directions, is shown as the vertical direction in the orientation of FIGS. 3-4, and is indicated at "TR" in FIGS. 3-4. As shown in FIGS. 3-4, in order to accommodate the cast saw's 100 varying transverse length, at least a portion of the distal body end portion 224, and correspondingly a portion of the interior cavity 336 at the distal body end portion 224, may have a greater transverse length than the proximal body end portion 222, and correspondingly the interior cavity 336 at the proximal body end portion 222.

The obscuring cover 216 may include at least one securing member 348, 350 that is configured to removably engage an exterior portion 352, 354 of the cast saw 100 to removably connected the obscuring cover 216 to the cast saw 100. The securing member 348, 350 may be at least partially located internal to and/or adjacent to the interior cavity 336. For example, the securing member 348, 350 may be in the interior cavity 336, on or extend from a lateral edge 356 of the obscuring cover 216 that is adjacent the lateral cover opening 342, on or extend from a longitudinal edge 358 of the obscuring cover 216 that is adjacent the longitudinal opening 344, may extend from or be located at any other portion of the obscuring cover 216 so that at least a portion of the securing member 348, 350 is internal to or adjacent to the interior cavity 232, or any combination thereof. The securing member 348, 350 may be any mechanism that provides a snap-fit engagement, a press-fit engagement, a magnetic engagement, an adhesive engagement, a frictional engagement, a screw and nut engagement, a hook and loop engagement, any other suitable engagement, or any combination thereof, to the cast saw 100. The shape, number, type, and/or size of the securing member(s) 348, 350 can be application dependent. The shape, number, type, and/or size of the securing member(s) 348, 350 may be configured so that a single obscuring cover 216 can be connected to a variety of different saws/cast saws, or may be configured to produce a specialized obscuring cover 216 that is configured to be connected to a specific type of saw/cast saw.

As shown in FIGS. 3-4, the at least one securing member 348, 350 may include a plurality of resilient clamps 348, 350 (shown here as first and second resilient clamps 348, 350) inside of the interior cavity 336 (though a portion of at least one resilient clamp 348, 350 may extend out from the interior cavity 336). Each of the first and second resilient clamps 348, 350 extends laterally from the upper portion 338 of the inner body surface 226 and has a clamp opening 360, 362 on one side. The clamp openings 360, 362 are dimensioned to permit the deformation of the resilient clamps 348, 350 at the clamp openings 360, 362 over exterior portions 352, 354 of the cast saw 100 to selectively engage and/or disengage the cast saw 100. In the example configuration of FIG. 3, the engagement between the first and second resilient clamps 348, 350 and the cast saw 100 is a snap-fit engagement. In other words, inner diameters of the first and second resilient clamps 348, 350 may expand from biased conditions when being engaged to exterior portions 352, 354 of the cast saw 100. Once the first and second resilient clamps 348, 350 have been placed over the exterior portions 352, 354 of the cast saw 100 so that the exterior portions 352, 354 are at least partially surrounded by the first and second resilient clamps 348, 350, the first and second resilient clamps 348, 350 may then "snap" substantially back to their biased conditions to engage the exterior portions 352, 354 of the cast saw 100. The engagement between the first and second resilient clamps 348, 350 and the cast saw 100, however, may alternatively be a frictional engagement.

As shown in FIG. 3, the first resilient clamp 348 may be configured to engage a first exterior portion 352 of the cast saw 100, while the second resilient clamp 350 may be configured to engage a second exterior portion 354 of the cast saw 100. The first exterior portion 352 of the cast saw 100 may contain the oscillating output drive train 108 and, thus, may be larger than the second exterior portion 354. Therefore, the inner diameter of the first resilient clamp 348 may be configured to engage the larger first exterior portion 352, and the inner diameter of the second resilient clamp 350 may be configured to engage the smaller second exterior portion 354.

The inner diameter of the first resilient clamp 348 may be greater than an outside diameter of the first exterior portion 352 of the cast saw 100 in order to permit the first resilient clamp 348 to engage the first exterior portion 352. Instead of having an inner diameter that is greater than the outside diameter of the first exterior portion 352 of the cast saw 100, the first resilient clamp 348 may have an inner diameter that is less than or equal to the outside diameter of the first exterior portion 352. In such case, the first resilient clamp 348 may be deformable so that the inner diameter is configured to expand when engaging the first exterior portion 352 of the cast saw 100. Having an expandable inner diameter allows the first resilient clamp 348 to adjust to a variety of saws/cast saws each having a first exterior portion 352 with a different outside diameter. Similarly, the inner diameter of the second resilient clamp 350 may be greater an outside diameter of the second exterior portion 354 of the cast saw 100, or may be less than or equal to the outside diameter of the second exterior portion 354.

The sequence of removing a cast 564 from a patient 566 presented below illustrates just one example sequence of operation. This sequence is not intended to limit the manner in which the obscuring cover 216 and/or the cast saw 100 are used to remove a cast 564 from a patient 566. Any of the steps detailed above can be performed before or after any other step depending on the configuration of the obscuring cover 216, the cast saw 100, and/or the procedure.

To remove a patient's cast 564, the obscuring cover 216 and the cast saw 100 as described above are be provided to an operator. At least a portion of the saw body 102 is inserted into the interior cavity 336 of the obscuring cover 216. At least a portion of the protective cover 110, when provided, may be inserted into the interior cavity 336 of the obscuring cover as the saw body 102 is inserted into the interior cavity 336. At least a portion of the saw blade 104 may also be inserted into the interior cavity 336 concurrently with the saw body 102 and/or the protective cover 110.

Figure 5:
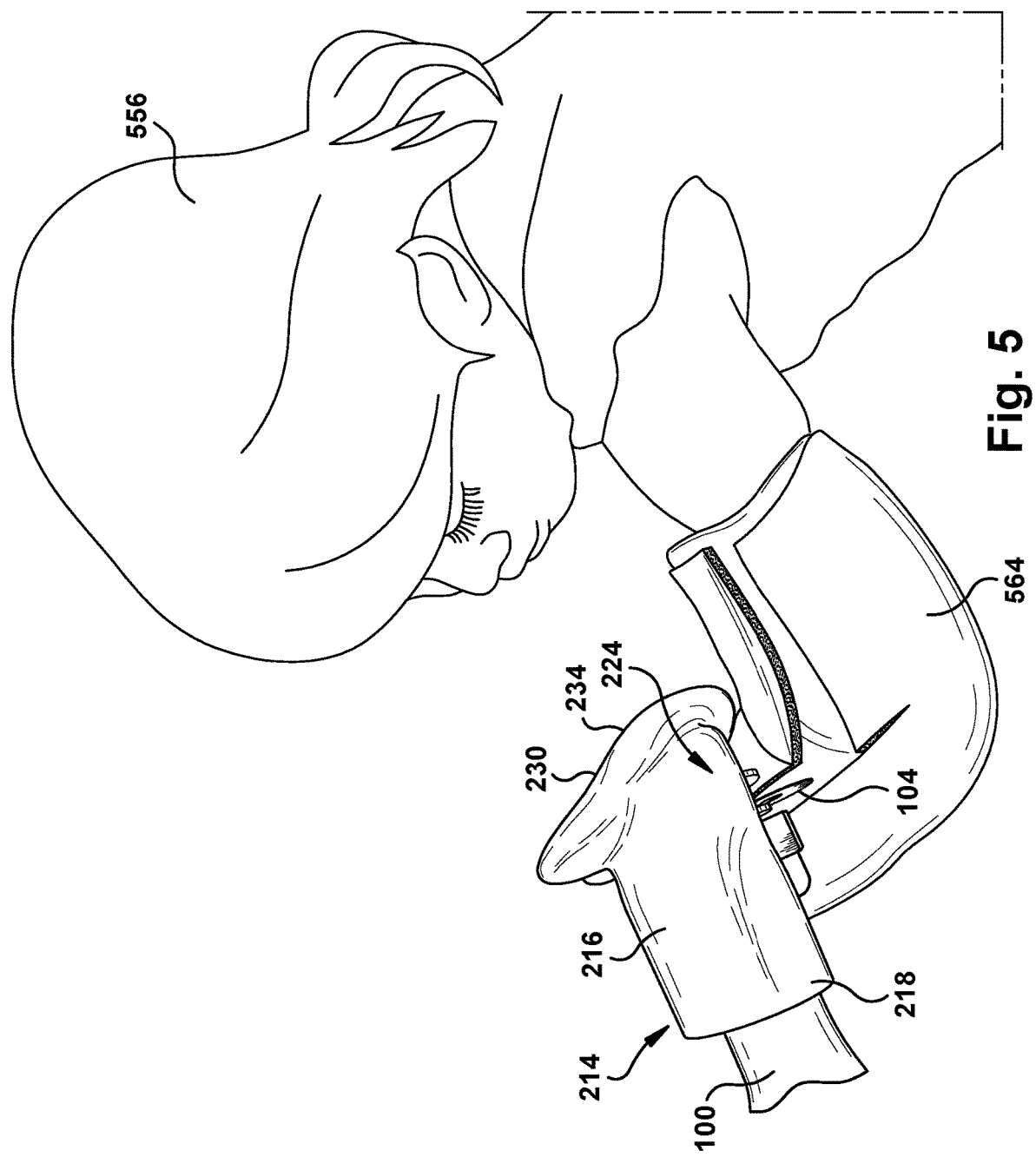
FIG. 5 is a side view of the aspect of FIG. 1, including the obscuring cover in an example use environment.

Once the cast saw 100 is inserted into the interior cavity 336, the obscuring cover 216 is connected to the cast saw 100 by engaging the first and second resilient clamps 348, 350 to the first and second exterior portions 352, 354 of the cast saw 100. The first and second resilient clamps 348, 350 can be engaged to the cast saw 100 at the same time, or in succession. As shown in FIG. 5, when the obscuring cover 216 is connected to the cast saw 100, the operator may cut the cast 564 of a patient 566 with the saw blade 104. In particular, the operator may actuate the motor 106 to drive the oscillating output drive train 108, which in turn oscillates the saw blade 104. The operator may then use the oscillating saw blade 104 to cut the patient's cast 564. After the operator is finished cutting the cast 564, the cut cast 564 may be removed from the patient 566.

At least a portion of the obscuring cover 216 is configured to at least partially visually obstruct the patient's view of the saw blade 104 from a predetermined patient use direction when the obscuring cover 216 is connected to the cast saw 100 and while the operator is cutting the cast 564. In particular, at least a portion of the cover head portion 230 may be configured to at least partially visually obstruct the patient's view of the saw blade 104. For example, as shown in FIG. 2, the cover head portion 230 may have a lateral head height 268 that is longer than a lateral body height 270 of the cover body portion 218. As shown in FIGS. 2 and 5, the lateral head height 270 and the increase in height of the cover head portion 230 over the cover body portion 218 at least partially restricts the patient's view of at least a portion of the saw blade 104 when the patient 566 is looking in the direction of the saw blade 104 from a predetermined patient use direction.

As shown in FIG. 2, the cover head portion 230 may also extend along a head axis 272. The head axis 272 may be at a predetermined angle α, such as an acute, obtuse, or right angle, relative to the longitudinal axis 220. As shown in FIGS. 2 and 5, the predetermined angle α is selected to at least partially restrict the patient's view of at least a portion of the saw blade 104 when the patient 566 is looking in the direction of the saw blade 104 from a predetermined patient use direction. The predetermined angle α shown in FIGS. 2 and 5 is an acute angle. The acute predetermined angle α tilts at least a portion of the cover head portion 230, e.g., the outer head surface 234, toward the predetermined patient use direction. The tilted cover head portion 230 together with the lateral head height 268 may help visually obstruct the patient's view of the saw blade 104.

Figure 6:
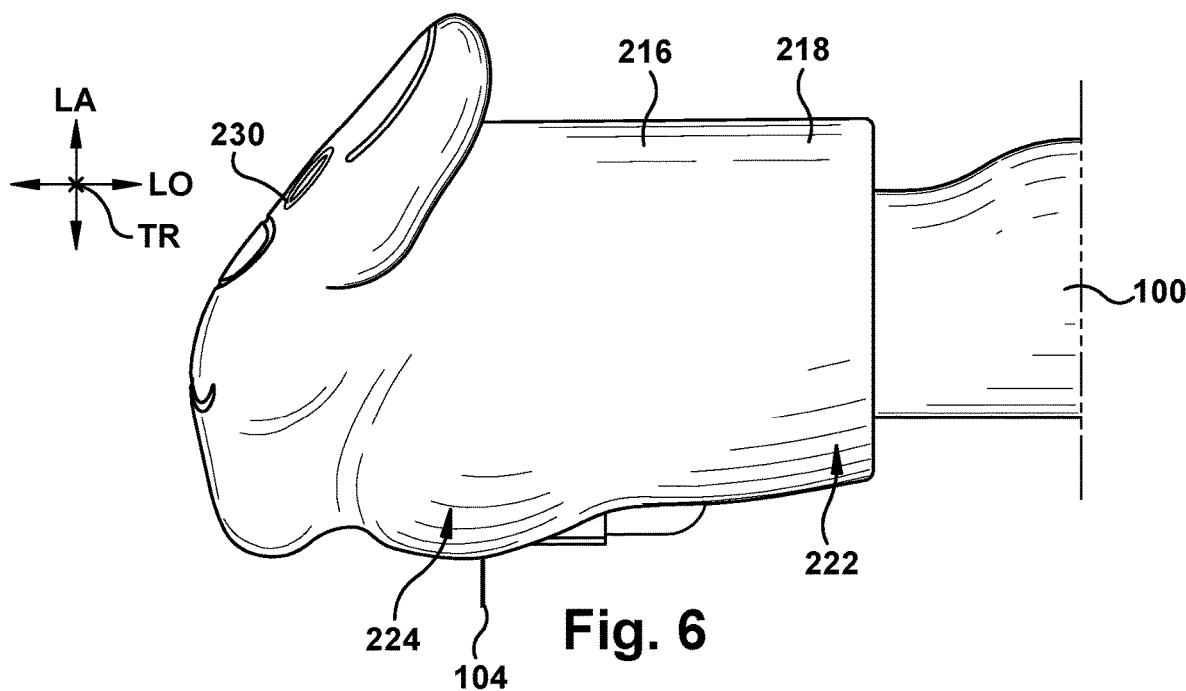
FIG. 6 is a side view of the aspect of FIG. 1, including a portion of the obscuring cover in an alternate configuration.

At least a portion of the cover body portion 218 may also be configured to at least partially visually obstruct the patient's view of the saw blade 104. For example, as shown in FIG. 6, the saw blade 104 may be adjacent the distal body end portion 224 when the obscuring cover 216 is connected to the cast saw 100. At least a portion of the distal body end portion 224 may thus be designed to extend further in the lateral direction than the proximal body end portion 222 in order to surround portions of the saw blade 104. Surrounding portions of the saw blade 104 with the distal body end portion 224 may help visually obstruct the patient's view of those portions saw blade 104 from a predetermined patient use direction.

Figure 7:
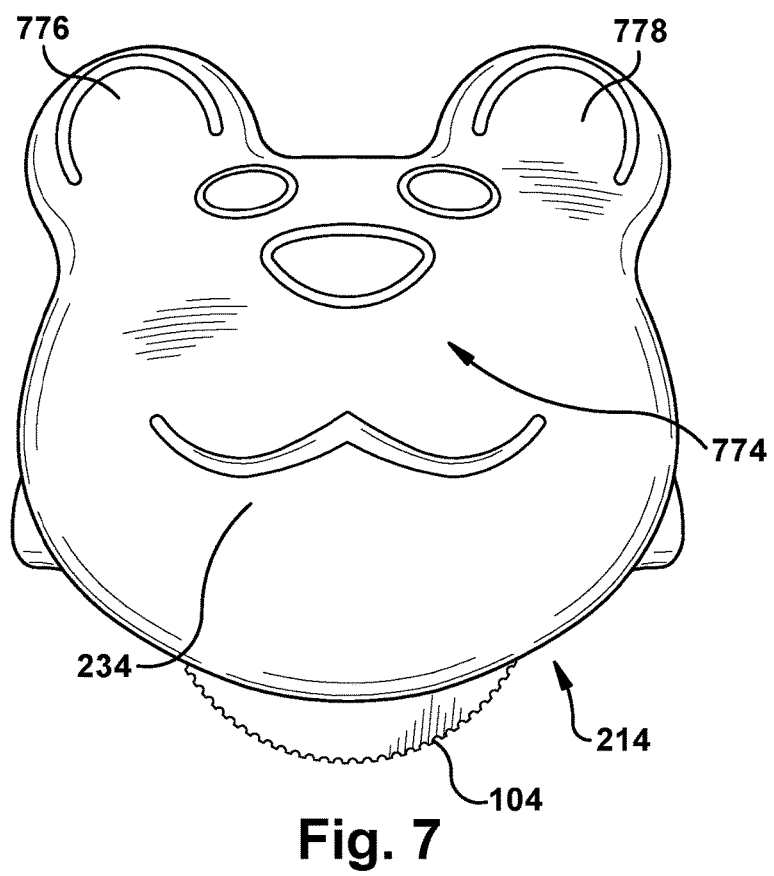
FIG. 7 is a front view of the aspect of FIG. 1.

As shown in FIG. 7, in addition to visually obstructing the patient's view of the saw blade 104, the obscuring cover 216 may include at least one aesthetically-pleasing design 774 formed thereon for calming, amusing, and/or distracting the patient 566 during the cast removal. The aesthetically-pleasing design 774 may include and/or be in the form of a realistic and/or stylized depiction of any of a fruit, a vegetable, a human or non-human animal, architecture, the sun or any other star, a planet, a cloud, a cartoon character, a word, any other aesthetically-pleasing or nonfunctional design, any component thereof, or any combination thereof. As shown in FIG. 7, the outer head surface 234 may include the aesthetically-pleasing design 774 formed thereon. The aesthetically-pleasing design 774 shown in FIG. 7 is in the form of a face of a non-human animal and, more particularly, in the form of a face of a bear.

The cover head portion 230 may also include one or more substantially laterally extending projections 776, 778 that may bear the design of an accessory feature of the aesthetically-pleasing design. The accessory feature may include and/or be in the form of an ear, a tusk, a trunk, a plant branch, a leaf, a flower, a paw, a hand, a talon, a fin, a tentacle, hair, a tail, a hat, headphones, any other accessory feature of the aesthetically-pleasing design, any protruding component thereof, or any combination thereof. As shown in FIG. 7, the cover head portion 230 may include two substantially laterally extending projections 776, 778 that are spaced apart from one another and bear the design of an accessory feature of the aesthetically-pleasing design on the outer head surface 234. The two projections 776, 778 of FIG. 7 are formed as the bear's ears.

Figure 8:
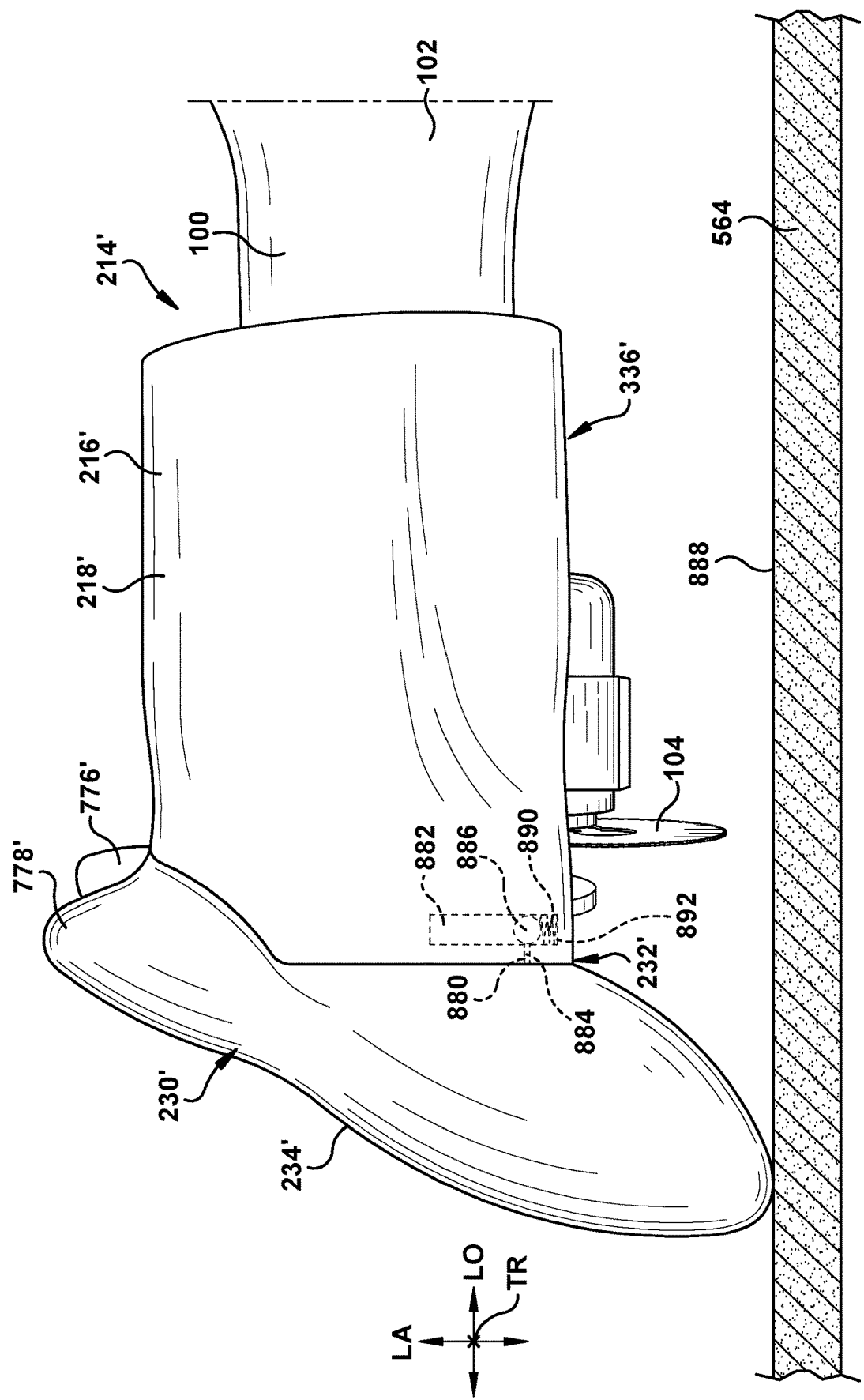
FIG. 8 is a side view of an obscuring cover for covering at least a portion of a saw according to another aspect of the present disclosure, including the obscuring cover in a first condition and in an example use environment.
Figure 9:
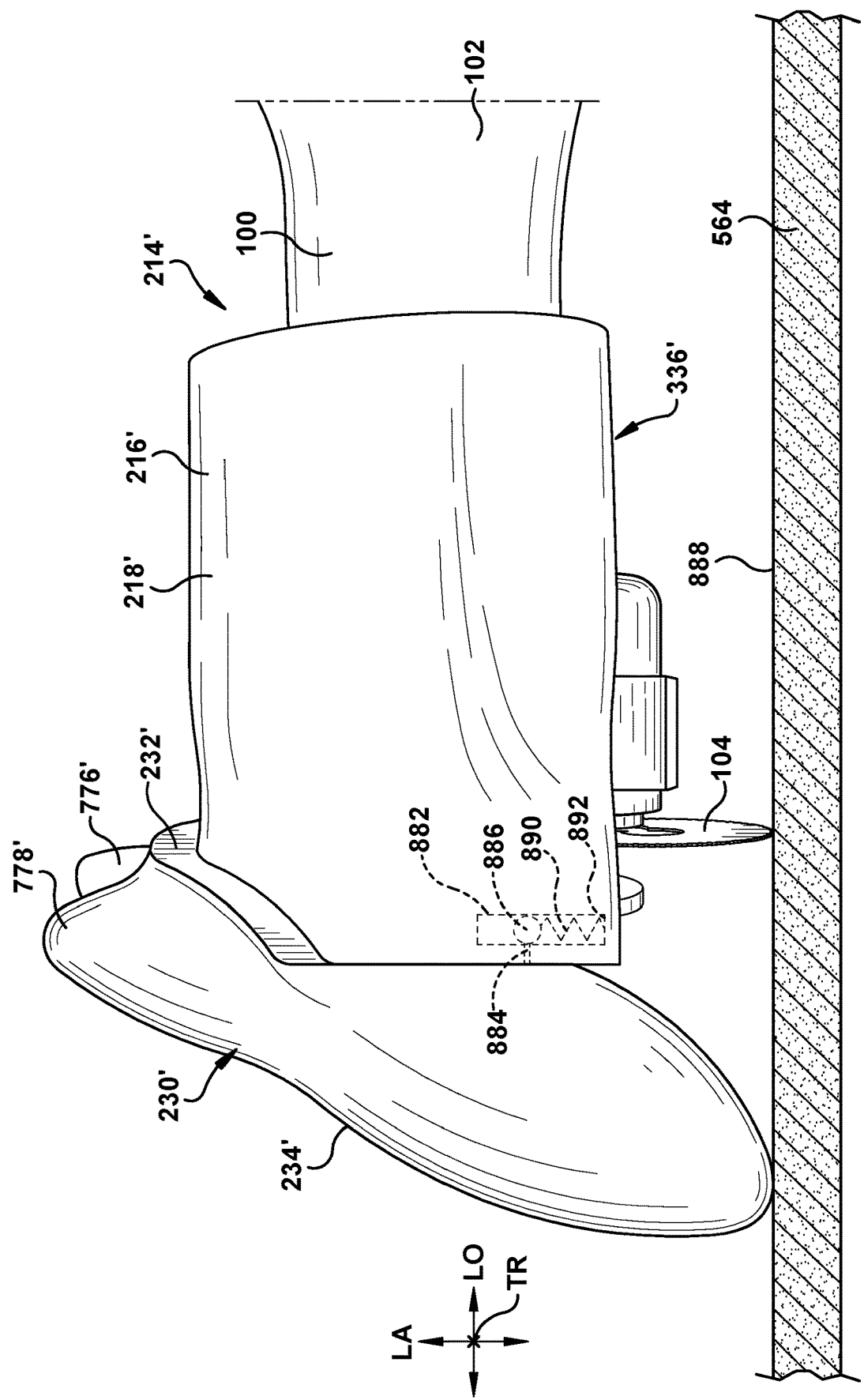
FIG. 9 is a side view of the aspect of FIG. 8, including the obscuring cover in a second condition and in the example use environment.

FIGS. 8-9 depict another example obscuring cover 216' designed in accordance with the teachings of the present disclosure. The obscuring cover 216' of FIGS. 8-9 is similar to the to the obscuring cover 216 of FIGS. 2-5 and therefore, structures that are the same as or similar to those described with reference to FIGS. 2-5 have the same reference numbers with the addition of a "prime" mark. Description of common elements and operation similar to those in the previously described the obscuring cover 216 of FIGS. 2-5 may not be repeated with respect to the obscuring cover 216' of FIGS. 8-9, but should instead be considered to be incorporated below by reference as appropriate. Furthermore, elements shown or described with respect to one of the example obscuring covers 216, 216' may be shared by the other of the example obscuring covers 216, 216' whether expressly stated, shown, or not.

The obscuring cover 216' of FIGS. 8-9 is similar to the obscuring cover 216 of FIGS. 2-5, except that the cover head portion 230' and the cover body portion 218' of the obscuring cover 216' of FIGS. 8-9 are mutually connected so as to permit selective lateral movement of the cover head portion 230' relative to the cover body portion 218'. Therefore, the cover head portion 230' and the cover body portion 218' may be connected to one another by one or more intervening elements that facilitate the selective relative lateral movement. For example, the cover head portion 230' may include at least one projection 880 that is configured to cooperate with at least one groove 882 in the cover body portion 218' to facilitate the selective relative movement. The at least one projection 880 and/or at least one groove 882 may be located internal or external to the interior cavity 336'. The projection 880 may include a first projection portion 884 extending longitudinally from the inner head surface 232'. A second projection portion 886 may be connected to an end of the first projection portion 884 and positioned in the groove 882. As shown in FIGS. 8-9, the second projection portion 886 may be configured to slide laterally along the groove 882 as the cover head portion 230' moves laterally relative to the cover body portion 218'.

As shown in FIG. 8, the cover head portion 230' has a biased condition in which the cover head portion 230' may engage an exterior cast surface 888, while the saw blade 104 is spaced from the exterior cast surface 886. The cover head portion 230' may be biased to the biased condition by at least one biasing member 890, such as, but not limited to, a spring. One end of the spring 890 may be connected to the projection 880, while another end of the spring 890 may be connected to a portion of the cover body portion 218'. For example, one spring end may be connected to the second projection portion 886, while tan opposite spring end may be connected to an edge 892 of the cover body portion 218' that at least partially surrounds and/or defines the groove 882.

As shown in FIG. 9, after the cover head portion 230' engages the exterior cast surface 888, the operator may apply a force to the obscuring cover 216' to urge the saw blade 104 laterally downward (in the orientation of FIG. 9) toward the exterior cast surface 888 in order to cut the cast 564. As the saw blade 104 is urged laterally downward, the cover head portion 230' is urged laterally upward (in the orientation of FIG. 9) relative to the cover body portion 218' by the exterior cast surface 888 and against the bias of the spring 890. At the same time, the second projection portion 886 slides laterally upward along the groove 882 and tensions the spring 890. Once the operator stops applying the force, the cover head portion 230' may spring back to the biased condition.

Although the intervening elements that facilitate the selective relative lateral movement of the cover head portion 230' relative to the cover body portion 218' are described as being at least one projection 880, at least one groove 882, and at least one biasing member 890, the obscuring cover 216' may include any feature or combination of features that facilitate the selective relative lateral movement.

Although the obscuring covers 216, 216' have been described and/or shown as being connected to a cast saw 100 and used during a cast removal procedure, each of the obscuring covers 216, 216' may be adapted to be connected to any type of saw, power tool, hand tool, surgical tool, or any combination thereof, for use with the connected saw/tool.

Although the cast saw 100 has been described as having an oscillating saw blade 104, the cast saw 100 may have a saw blade that moves in any manner for selectively cutting a cast. For example, the cast saw 100 may have a rotating saw blade that selectively rotates about a rotational axis. Furthermore, the cast saw 100 may be configured with no protective cover 110. In such a configuration, the obscuring cover 216, 216', when connected to the cast saw 100, may at least partially act as a protective cover.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. An obscuring cover for covering at least a portion of a saw that includes a saw body and a saw blade attached to the saw body, the obscuring cover comprising:
    an interior cavity defined by at least one inner surface of the obscuring cover, the interior cavity being configured to removably receive at least a portion of the saw body;
    a cover body portion having an inner body surface that defines at least a portion of the interior cavity;
    a cover head portion longitudinally adjacent to the cover body portion and configured to at least partially visually obstruct the subject's view of the saw blade, the cover head portion having oppositely facing inner and outer head surfaces, the inner head surface defining at least a portion of the interior cavity, the outer head surface being configured for visual exposure to the subject when the saw is in use; and at least one securing member at least partially located at least one of internal to and adjacent to the interior cavity, the at least one securing member being configured to removably engage an exterior portion of the saw to removably connect the obscuring cover to the saw;

wherein at least a portion of the obscuring cover is configured to at least partially visually obstruct a subject's view of the saw blade when the obscuring cover is connected to the saw.

2. The obscuring cover of claim 1, wherein the cover body portion extends along a longitudinal axis of the obscuring cover, the cover head portion extending substantially along a head axis, the head axis being at a predetermined angle relative to the longitudinal axis.

3. The obscuring cover of claim 1, wherein the cover head portion has a lateral head height that is longer than a lateral body height of the cover body portion.

4. The obscuring cover of claim 1, wherein the cover body portion has a proximal body end portion and a distal body end portion, the distal body end portion having the cover head portion attached thereto, at least a portion of the distal body end portion extending further in the lateral direction than does the proximal body end portion.

5. The obscuring cover of claim 1, wherein the outer head surface includes an aesthetically-pleasing design formed thereon.

6. The obscuring cover of claim 5, wherein the aesthetically-pleasing design is in the form of a face of a non-human animal.

7. The obscuring cover of claim 5, wherein the cover head portion includes two substantially laterally extending projections that are spaced apart from one another, the projections bearing the design of an accessory feature of the non-human animal.

8. The obscuring cover of claim 1, wherein the cover head portion and the cover body portion are mutually connected so as to resist relative movement.

9. The obscuring cover of claim 1, wherein the cover head portion and the cover body portion are mutually connected so as to permit selective movement of the cover head portion relative to the cover body portion.

10. The obscuring cover of claim 1, wherein the interior cavity includes a lateral cover opening in the obscuring cover, the interior cavity being accessible through the lateral cover opening.

11. The obscuring cover of claim 10, wherein the interior cavity includes a longitudinal cover opening in the obscuring cover, the interior cavity being accessible through the longitudinal cover opening, the saw body being selectively inserted through the lateral cover opening into the interior cavity, a portion of the saw body extending through the longitudinal cover opening when the saw body is received in the interior cavity.

12. The obscuring cover of claim 1, wherein the saw includes a protective cover surrounding at least a portion of the saw blade to at least partially prevent contact between the saw blade and a non-target area, at least a portion of the protective cover being configured to be removably received in the interior cavity.

13. The obscuring cover of claim 1, wherein the saw is a cast saw.

14. The obscuring cover of claim 1, wherein the at least one securing mechanism includes a resilient clamp having a clamp opening on one side configured to selectively permit deformation of the resilient clamp at the clamp opening over the exterior portion of the saw to selectively engage and/or disengage the saw.

15. The obscuring cover of claim 14, wherein the engagement between the resilient clamp and the saw is a snap-fit engagement.

16. The obscuring cover of claim 14, wherein the at least one securing mechanism includes a plurality of resilient clamps in the interior cavity, at least one of the resilient clamps being configured to engage a first exterior portion of the saw, and at least one of the resilient clamps being configured to engage a second exterior portion of the saw, the first exterior portion being larger than the second exterior portion.

17. A cast removal kit, comprising:
a cast saw having a saw body, a saw blade attached to the saw body, and a motor actuatable to selectively move the saw blade relative to the saw body for cutting a portion of a cast, the cast saw having a protective cover attached to the saw body and surrounding at least a portion of the saw blade so as to at least partially prevent contact between the saw blade and a non-target area; and
the obscuring cover of claim 1.

18. A method for removing a cast from a subject, the method comprising:
providing the obscuring cover of claim 1;
providing a cast saw that includes a saw body and a saw blade attached to the saw body;
inserting at least a portion of the saw body into the interior cavity of the obscuring cover;
connecting the obscuring cover to the cast saw by engaging the at least one securing member to an exterior portion of the cast saw;
with the obscuring cover connected to the cast saw, cutting the cast with the saw blade;
concurrently with cutting the cast, obstructing the subject's view of the saw blade with the obscuring cover; and
removing the cut cast from the subject.

19. The method of claim 18, wherein the cast saw includes a protective cover surrounding at least a portion of the saw blade to at least partially prevent contact between the saw blade and a non-target area, the method further comprising:
concurrently with inserting at least a portion of the saw body into the interior cavity of the obscuring cover, inserting at least a portion of the protective cover into the interior cavity of the obscuring cover.

* * * * *